(12) United States Patent
McAuley et al.

(10) Patent No.: US 7,566,319 B2
(45) Date of Patent: Jul. 28, 2009

(54) TRACTION BALLOON

(75) Inventors: Steven A. McAuley, Chanhassen, MN (US); Karen M. Cheves, Escondido, CA (US); Loren M. Crow, Las Mesa, CA (US); Gregory S. Kelley, San Diego, CA (US); Herbert R. Radisch, Jr., San Diego, CA (US); Ricardo David Roman, San Diego, CA (US); Show-Mean Wu, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 141 days.

(21) Appl. No.: 10/828,572

(22) Filed: Apr. 21, 2004

(65) Prior Publication Data

US 2005/0240212 A1 Oct. 27, 2005

(51) Int. Cl.
*A61M 29/00* (2006.01)

(52) U.S. Cl. .............. 604/103.08; 604/96.01; 604/103.06

(58) Field of Classification Search ........... 604/194, 604/96.01, 103.03, 103.05, 103.08, 915
See application file for complete search history.

(56) References Cited

U.S. PATENT DOCUMENTS

| 2,816,552 A | 12/1957 | Hoffman |
| 3,174,851 A | 3/1965 | Buehler et al. |
| 3,351,463 A | 11/1967 | Rozner et al. |
| 3,635,223 A | 1/1972 | Klieman |
| 3,749,085 A | 7/1973 | Willson et al. |
| 3,753,700 A | 8/1973 | Harrison et al. |
| 3,990,453 A | 11/1976 | Douvas et al. |
| 4,140,126 A | 2/1979 | Choudhury |
| 4,141,364 A | 2/1979 | Schultze |
| 4,263,236 A | 4/1981 | Briggs et al. |
| 4,273,128 A | 6/1981 | Lary |
| 4,292,974 A | 10/1981 | Fogarty et al. |
| 4,406,656 A | 9/1983 | Hattler et al. |
| 4,465,072 A | 8/1984 | Taheri |
| 4,490,421 A | 12/1984 | Levy |
| 4,572,186 A | 2/1986 | Gould et al. |

(Continued)

FOREIGN PATENT DOCUMENTS

DE 34 00 416 A1 7/1985

(Continued)

OTHER PUBLICATIONS

Lary, Banning G., et al., "A Method for Creating a Coronary-Myocardial Artery," *Surgery*, Jun. 1966, vol. 59, No. 6, pp. 1061-1064.

(Continued)

*Primary Examiner*—Nicholas D Lucchesi
*Assistant Examiner*—Laura A Bouchelle
(74) *Attorney, Agent, or Firm*—Crompton, Seager & Tufte, LLC

(57) ABSTRACT

Balloon catheters and methods of making and using the same. A balloon catheter may include a catheter shaft and a balloon coupled thereto. A traction member may be coupled to the balloon catheter adjacent the balloon and may extend along a portion or all of the length of the balloon. The traction member can improve traction between the balloon and a target site.

1 Claim, 10 Drawing Sheets

U.S. PATENT DOCUMENTS

| | | |
|---|---|---|
| 4,574,781 A | 3/1986 | Chin |
| 4,608,984 A | 9/1986 | Fogarty |
| 4,627,436 A | 12/1986 | Leckrone |
| 4,685,458 A | 8/1987 | Leckrone |
| 4,686,982 A | 8/1987 | Nash |
| 4,696,667 A | 9/1987 | Masch |
| 4,705,517 A | 11/1987 | DiPisa, Jr. |
| 4,723,549 A | 2/1988 | Wholey et al. |
| 4,728,319 A | 3/1988 | Masch |
| 4,747,405 A | 5/1988 | Leckrone |
| 4,748,982 A | 6/1988 | Horzewski et al. |
| 4,781,186 A | 11/1988 | Simpson et al. |
| 4,784,636 A | 11/1988 | Rydell |
| 4,787,388 A | 11/1988 | Hofmann |
| 4,790,813 A | 12/1988 | Kensey |
| 4,793,348 A | 12/1988 | Palmaz |
| 4,796,629 A | 1/1989 | Grayzel |
| 4,799,479 A | 1/1989 | Spears |
| RE32,983 E | 7/1989 | Levy |
| 4,867,157 A | 9/1989 | McGurk-Burleson et al. |
| 4,886,061 A | 12/1989 | Fischell et al. |
| 4,887,613 A | 12/1989 | Farr et al. |
| 4,896,669 A | 1/1990 | Bhate et al. |
| 4,909,781 A | 3/1990 | Husted |
| 4,921,483 A | 5/1990 | Wijay et al. |
| 4,921,484 A | 5/1990 | Hillstead |
| 4,936,845 A | 6/1990 | Stevens |
| 4,960,410 A | 10/1990 | Pinchuk |
| 4,966,604 A | 10/1990 | Reiss |
| 4,986,807 A | 1/1991 | Farr |
| 4,994,018 A | 2/1991 | Saper |
| RE33,561 E | 3/1991 | Levy |
| 5,009,659 A | 4/1991 | Hamlin et al. |
| 5,015,231 A | 5/1991 | Keith et al. |
| 5,030,201 A | 7/1991 | Palestrant |
| 5,041,125 A | 8/1991 | Montano, Jr. |
| 5,042,985 A | 8/1991 | Elliott et al. |
| 5,047,040 A | 9/1991 | Simpson et al. |
| 5,053,007 A | 10/1991 | Euteneuer |
| 5,053,044 A | 10/1991 | Mueller et al. |
| 5,071,424 A | 12/1991 | Reger |
| 5,074,841 A | 12/1991 | Ademovic et al. |
| 5,074,871 A | 12/1991 | Groshong |
| 5,078,722 A | 1/1992 | Stevens |
| 5,078,725 A | 1/1992 | Enderle et al. |
| 5,084,010 A | 1/1992 | Plaia et al. |
| 5,085,662 A | 2/1992 | Willard |
| 5,087,246 A | 2/1992 | Smith |
| 5,087,265 A | 2/1992 | Summers |
| 5,100,424 A | 3/1992 | Jang et al. |
| 5,100,425 A | 3/1992 | Fischell et al. |
| 5,102,390 A | 4/1992 | Crittenden et al. |
| 5,102,403 A | 4/1992 | Alt |
| 5,116,318 A | 5/1992 | Hillstead |
| 5,135,482 A | 8/1992 | Neracher |
| 5,147,302 A | 9/1992 | Euteneuer et al. |
| 5,156,594 A | 10/1992 | Keith |
| 5,156,610 A | 10/1992 | Reger |
| 5,158,564 A | 10/1992 | Schnepp-Pesch et al. |
| 5,176,693 A | 1/1993 | Pannek, Jr. |
| 5,178,625 A | 1/1993 | Groshong |
| 5,180,368 A | 1/1993 | Garrison |
| 5,192,291 A | 3/1993 | Pannek, Jr. |
| 5,196,024 A | 3/1993 | Barath |
| 5,196,025 A | 3/1993 | Ranalletta et al. |
| 5,209,749 A | 5/1993 | Buelna |
| 5,209,799 A | 5/1993 | Vigil |
| 5,221,261 A * | 6/1993 | Termin et al. ............... 604/104 |
| 5,224,945 A | 7/1993 | Pannek, Jr. |
| 5,226,430 A | 7/1993 | Spears et al. |
| 5,226,887 A | 7/1993 | Farr et al. |
| 5,226,909 A | 7/1993 | Evans et al. |
| 5,242,396 A | 9/1993 | Evard |
| 5,248,311 A | 9/1993 | Black et al. |
| 5,250,059 A | 10/1993 | Andreas et al. |
| 5,295,959 A | 3/1994 | Gurbel et al. |
| 5,300,025 A | 4/1994 | Wantink |
| 5,312,425 A | 5/1994 | Evans et al. |
| 5,318,576 A | 6/1994 | Plassche, Jr. et al. |
| 5,320,634 A | 6/1994 | Vigil et al. |
| 5,328,472 A | 7/1994 | Steinke et al. |
| 5,336,234 A | 8/1994 | Vigil et al. |
| 5,342,301 A | 8/1994 | Saab |
| 5,342,307 A | 8/1994 | Euteneuer et al. |
| 5,346,505 A | 9/1994 | Leopold |
| 5,350,361 A | 9/1994 | Tsukashima et al. |
| 5,372,601 A | 12/1994 | Lary |
| 5,395,361 A | 3/1995 | Fox et al. |
| 5,399,164 A | 3/1995 | Snoke et al. |
| 5,403,334 A | 4/1995 | Evans et al. |
| 5,409,454 A | 4/1995 | Fischell et al. |
| 5,411,466 A | 5/1995 | Hess |
| 5,411,478 A | 5/1995 | Stillabower |
| 5,415,654 A | 5/1995 | Daikuzono |
| 5,417,653 A | 5/1995 | Sahota et al. |
| 5,417,703 A | 5/1995 | Brown et al. |
| 5,423,745 A | 6/1995 | Todd et al. |
| 5,425,711 A | 6/1995 | Ressemann et al. |
| 5,425,712 A | 6/1995 | Goodin |
| 5,437,659 A | 8/1995 | Leckrone |
| 5,441,510 A | 8/1995 | Simpson et al. |
| 5,449,343 A | 9/1995 | Samson et al. |
| 5,456,666 A | 10/1995 | Campbell et al. |
| 5,456,681 A | 10/1995 | Hajjar |
| 5,458,572 A | 10/1995 | Campbell et al. |
| 5,478,319 A | 12/1995 | Campbell et al. |
| 5,484,449 A * | 1/1996 | Amundson et al. .......... 606/108 |
| 5,487,730 A | 1/1996 | Marcadis et al. |
| 5,496,308 A | 3/1996 | Brown et al. |
| 5,507,760 A | 4/1996 | Wynne et al. |
| 5,507,761 A | 4/1996 | Duer |
| 5,522,818 A | 6/1996 | Keith et al. |
| 5,522,825 A | 6/1996 | Kropf et al. |
| 5,538,510 A | 7/1996 | Fontirroche et al. |
| 5,542,924 A | 8/1996 | Snoke et al. |
| 5,549,556 A | 8/1996 | Ndondo-Lay et al. |
| 5,554,121 A | 9/1996 | Ainsworth et al. |
| 5,556,405 A | 9/1996 | Lary |
| 5,556,408 A | 9/1996 | Farhat |
| 5,569,277 A | 10/1996 | Evans et al. |
| 5,571,087 A | 11/1996 | Ressemann et al. |
| 5,616,149 A | 4/1997 | Barath |
| 5,628,761 A | 5/1997 | Rizik |
| 5,643,209 A | 7/1997 | Fugoso et al. |
| 5,643,296 A | 7/1997 | Hundertmark et al. |
| 5,649,941 A | 7/1997 | Lary |
| 5,662,671 A | 9/1997 | Barbut et al. |
| 5,669,920 A | 9/1997 | Conley et al. |
| 5,681,336 A | 10/1997 | Clement et al. |
| 5,697,944 A | 12/1997 | Lary |
| 5,713,913 A | 2/1998 | Lary et al. |
| 5,718,684 A | 2/1998 | Gupta |
| 5,720,724 A | 2/1998 | Ressemann et al. |
| 5,720,726 A * | 2/1998 | Marcadis et al. ....... 604/103.08 |
| 5,728,123 A | 3/1998 | Lemelson et al. |
| 5,743,875 A | 4/1998 | Sirhan et al. |
| 5,759,191 A | 6/1998 | Barbere |
| 5,769,819 A | 6/1998 | Schwab et al. |
| 5,769,865 A | 6/1998 | Kermode et al. |
| 5,792,158 A | 8/1998 | Lary |
| 5,797,935 A | 8/1998 | Barath |
| 5,800,450 A | 9/1998 | Lary et al. |
| 5,820,594 A | 10/1998 | Fontirroche et al. |
| 5,824,173 A | 10/1998 | Fontirroche et al. |

| | | | |
|---|---|---|---|
| 5,827,201 A | 10/1998 | Samson et al. | |
| 5,827,225 A | 10/1998 | Ma Schwab | |
| 5,827,310 A | 10/1998 | Mann et al. | |
| 5,895,402 A | 4/1999 | Hundertmark et al. | |
| 5,921,958 A | 7/1999 | Ressemann et al. | |
| 5,928,193 A * | 7/1999 | Campbell | 604/96.01 |
| 5,931,819 A | 8/1999 | Fariabi | |
| 5,993,469 A | 11/1999 | McKenzie et al. | |
| 5,997,557 A | 12/1999 | Barbut et al. | |
| 6,024,722 A | 2/2000 | Rau et al. | |
| 6,030,371 A | 2/2000 | Pursley | |
| 6,039,699 A | 3/2000 | Viera | |
| 6,066,149 A | 5/2000 | Samson et al. | |
| 6,068,623 A | 5/2000 | Zadno-Azizi et al. | |
| 6,110,192 A | 8/2000 | Ravenscroft et al. | |
| 6,117,153 A | 9/2000 | Lary et al. | |
| 6,139,510 A | 10/2000 | Palermo | |
| 6,142,975 A | 11/2000 | Jalisi et al. | |
| 6,165,140 A | 12/2000 | Ferrera | |
| 6,165,167 A | 12/2000 | Delaloye | |
| 6,165,292 A | 12/2000 | Abrams et al. | |
| 6,168,571 B1 | 1/2001 | Solar et al. | |
| 6,179,851 B1 | 1/2001 | Barbut et al. | |
| 6,190,332 B1 | 2/2001 | Muni et al. | |
| 6,193,686 B1 | 2/2001 | Estrada et al. | |
| 6,213,957 B1 | 4/2001 | Milliman et al. | |
| 6,217,549 B1 | 4/2001 | Selmon et al. | |
| 6,217,567 B1 | 4/2001 | Zadno-Azizi et al. | |
| 6,221,006 B1 | 4/2001 | Dubrul et al. | |
| 6,241,690 B1 | 6/2001 | Burkett et al. | |
| 6,254,550 B1 | 7/2001 | McNamara et al. | |
| 6,258,099 B1 * | 7/2001 | Mareiro et al. | 606/108 |
| 6,258,108 B1 | 7/2001 | Lary | |
| 6,264,633 B1 * | 7/2001 | Knorig | 604/102.01 |
| 6,283,743 B1 | 9/2001 | Traxler et al. | |
| 6,306,105 B1 | 10/2001 | Rooney et al. | |
| 6,306,151 B1 | 10/2001 | Lary | |
| 6,309,399 B1 | 10/2001 | Barbut et al. | |
| 6,344,029 B1 | 2/2002 | Estrada et al. | |
| 6,355,016 B1 | 3/2002 | Bagaoisan et al. | |
| 6,383,146 B1 | 5/2002 | Klint | |
| 6,387,075 B1 | 5/2002 | Stivland et al. | |
| 6,394,995 B1 | 5/2002 | Solar et al. | |
| 6,398,798 B2 | 6/2002 | Selmon et al. | |
| 6,409,863 B1 | 6/2002 | Williams et al. | |
| 6,425,882 B1 | 7/2002 | Vigil | |
| 6,450,988 B1 * | 9/2002 | Bradshaw | 604/96.01 |
| 6,471,673 B1 | 10/2002 | Kasterhofer | |
| 6,471,713 B1 | 10/2002 | Vargos et al. | |
| 6,533,754 B1 | 3/2003 | Hisamatsu et al. | |
| 6,544,276 B1 | 4/2003 | Azizi | |
| 6,562,062 B2 | 5/2003 | Jenusaitis et al. | |
| 6,602,265 B2 | 8/2003 | Dubrul et al. | |
| 6,626,861 B1 * | 9/2003 | Hart et al. | 604/96.01 |
| 6,632,231 B2 | 10/2003 | Radisch, Jr. | |
| 6,663,589 B1 * | 12/2003 | Halevy | 604/96.01 |
| 7,186,237 B2 * | 3/2007 | Meyer et al. | 604/96.01 |
| 2002/0010489 A1 * | 1/2002 | Grayzel et al. | 606/194 |
| 2003/0163148 A1 | 8/2003 | Wang et al. | |
| 2004/0243158 A1 | 12/2004 | Konstantino et al. | |

FOREIGN PATENT DOCUMENTS

| | | |
|---|---|---|
| DE | 34 02 573 A1 | 8/1985 |
| DE | 35 19 626 A1 | 12/1986 |
| EP | 0 291 170 A1 | 11/1988 |
| EP | 0 414 350 A1 | 2/1991 |
| EP | 0 784 966 B1 | 7/1997 |
| EP | 0 792 656 A1 | 9/1997 |
| GB | 1 547 328 | 6/1979 |
| WO | WO 90/07909 A1 | 7/1990 |
| WO | WO 91/17714 A1 | 11/1991 |

OTHER PUBLICATIONS

Lary, Banning G., "An Epicaridal Purse String Suture for Closing Coronary Arteriotomy," *The American Surgeon*, Mar. 1967, vol. 33, No. 3, pp. 213-214.

Lary, Banning G., "Coronary Artery Incision and Dilation," *Archives of Surgery*, Dec. 1980, vol. 115, pp. 1478-1480.

Lary, Banning G., "Coronary Artery Resection and Replacement by a Blood Conduit," *Surgery*, Apr. 1969, vol. 65, No. 4, pp. 584-589.

Lary, Banning G., "Effect of Endocardial Incisions on Myocardial Blood Flow," *Archives of Surgery*, Sep. 1963, vol. 87, pp. 424-427.

Lary, B.G., "Experimental Maintenance of Life by Intravenous Oxygen, Preliminary Report," *Clinical Congress of the American College of Surgeons*, San Francisco, Nov. 5-9, 1951, pp. 30-35.

Lary, Banning G., et al., "Experimental Vein Angioplasty of the Circumflex Coronary Artery," *Journal of Surgical Research*, Sep. 1974, vol. 17, No. 3, pp. 210-214.

Lary, Banning G., "Method for Increasing the Diameter of Long Segments of the Coronary Artery," *The American Surgeon*, Jan. 1966, vol. 32, No. 1, pp. 33-35.

Lary, Banning G., et al., "Myocardial Revascularization Experiments Using the Epicardium," *Archives of Surgery*, Jan. 1969, vol. 98, pp. 69-72.

Lary, Banning G., "Onlay Vein Graft for the Correction of Coronary Artery Obstruction," *Surgery*, Apr. 1966, vol. 59, No. 4, pp. 547-551.

Lary, Banning G., "Surgery for Coronary Artery Disease," *Nursing Clinics of North America*, Sep. 1967, vol. 2, No. 3, pp. 537-542.

Lary, Banning G., et al., "The 'Coronary Myocardial Artery' for Coronary Artery Disease," *Diseases of the Chest*, Apr. 1996, vol. 49, No. 4, pp. 412-419.

U.S. Appl. No. 10/436,216, to Show-Mean Wu, filed May 12, 2003.

U.S. Appl. No. 10/447,766, to Show-Mean Steve Wu et al., filed May 29, 2003.

U.S. Appl. No. 10/821,237, to Gregory S. Kelley, filed Apr. 8, 2004.

Lary, Banning G., "A Method to Create and Correct Stenosis of a Coronary Artery," *Archives of Surgery*, Nov. 1966, vol. 93, pp. 828-830.

* cited by examiner

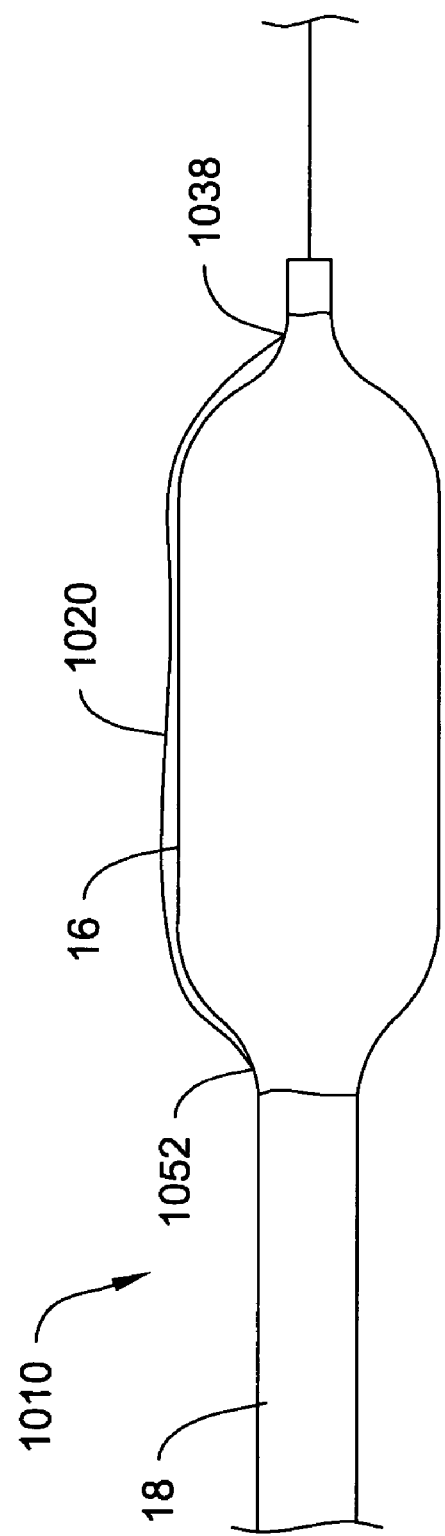

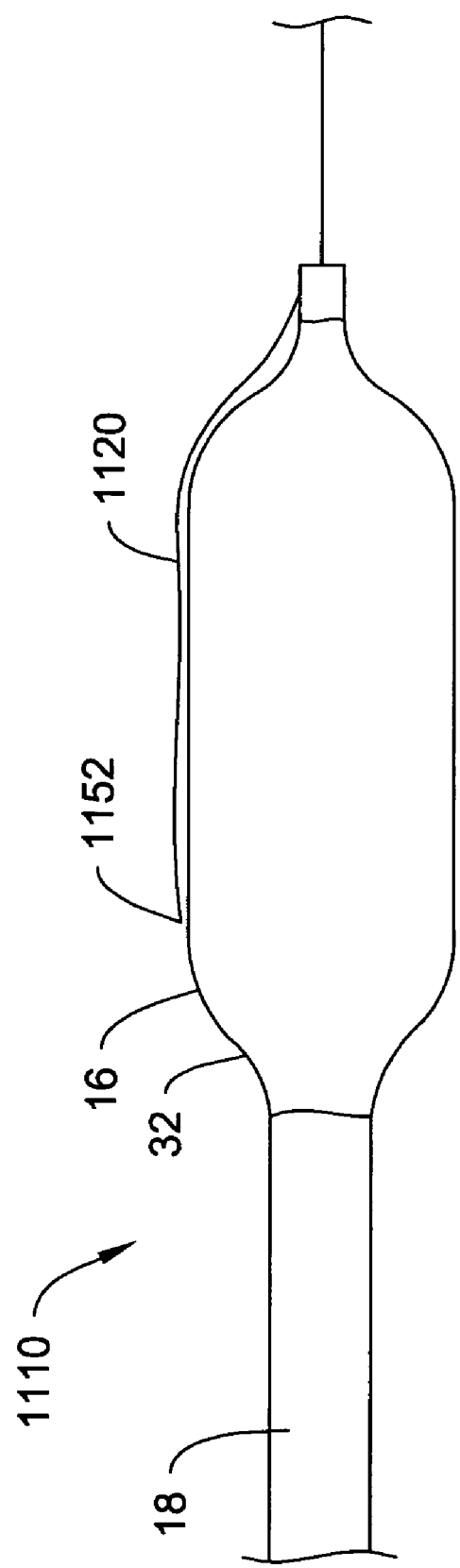

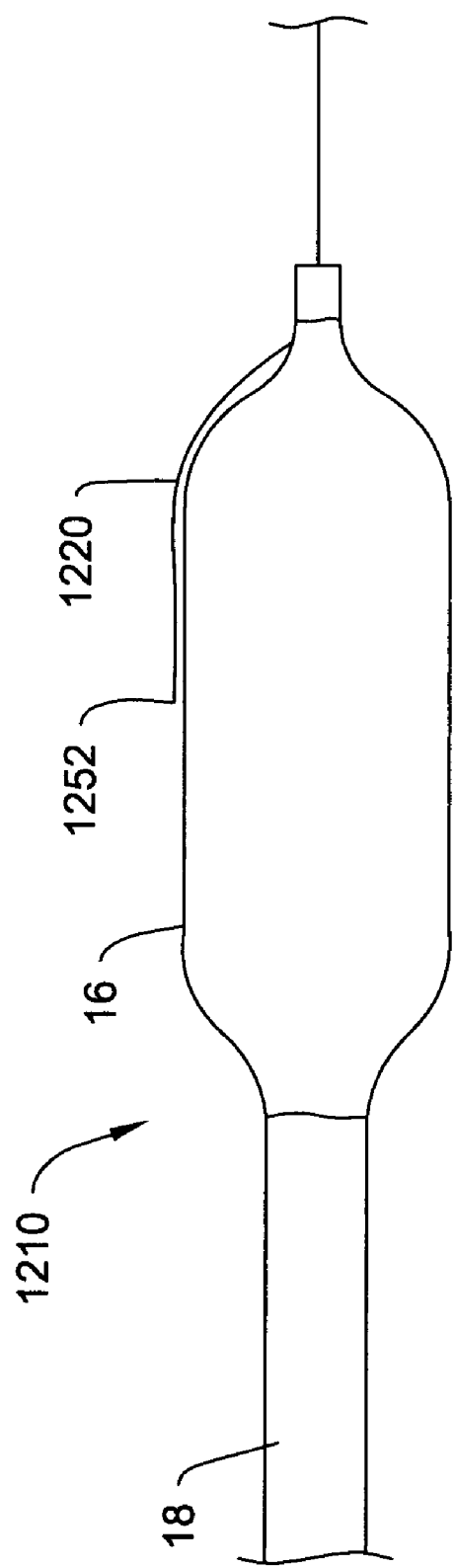

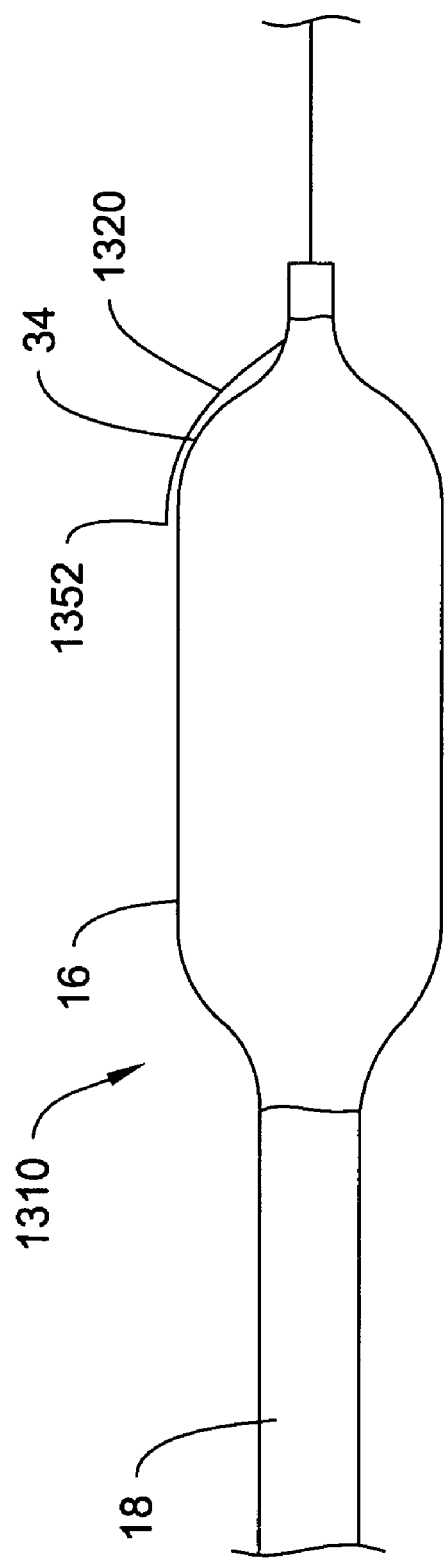

TRACTION BALLOON

FIELD OF THE INVENTION

The present invention pertains to angioplasty and angioplasty balloon catheters. More particularly, the present invention pertains to angioplasty balloon catheters that include a shaft or traction member disposed adjacent the balloon for increasing the traction between the balloon and a target site.

BACKGROUND OF THE INVENTION

Heart and vascular disease are major problems in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire so that the balloon is positioned adjacent a stenotic lesion. The balloon is then inflated and the restriction of the vessel is opened.

A wide variety of balloon catheters and angioplasty balloons exist, each with certain advantages and disadvantages. Some of these catheters include balloons that are highly lubricious, for example, so that they can easily navigate the vascular system. Although this lubricity is desirable for a number of reasons, it can sometimes cause a balloon to move during an interventional procedure or slip away from a lesion during the intervention. This could decrease the efficiency or the effectiveness of a procedure. There is an ongoing need for improved or refined balloon catheters.

SUMMARY

The present invention relates to angioplasty balloon catheters. In at least some embodiments, an example balloon catheter may include a catheter shaft having a balloon coupled thereto. A traction member may be coupled to the shaft and/or a portion of the balloon and extend along some or all of the length of the balloon. The traction member may, for example, improve traction between the balloon and a target site and may include one or more gripping members or a gripping region. These and other features are described in more detail below.

BRIEF DESCRIPTION OF THE DRAWINGS

FIG. 12 is a simplified schematic side view of another example catheter;

FIG. 13 is a simplified schematic side view of another example catheter;

FIG. 14 is a simplified schematic side view of another example catheter; and

FIG. 15 is a simplified schematic side view of another example catheter.

DETAILED DESCRIPTION

Figure 1:
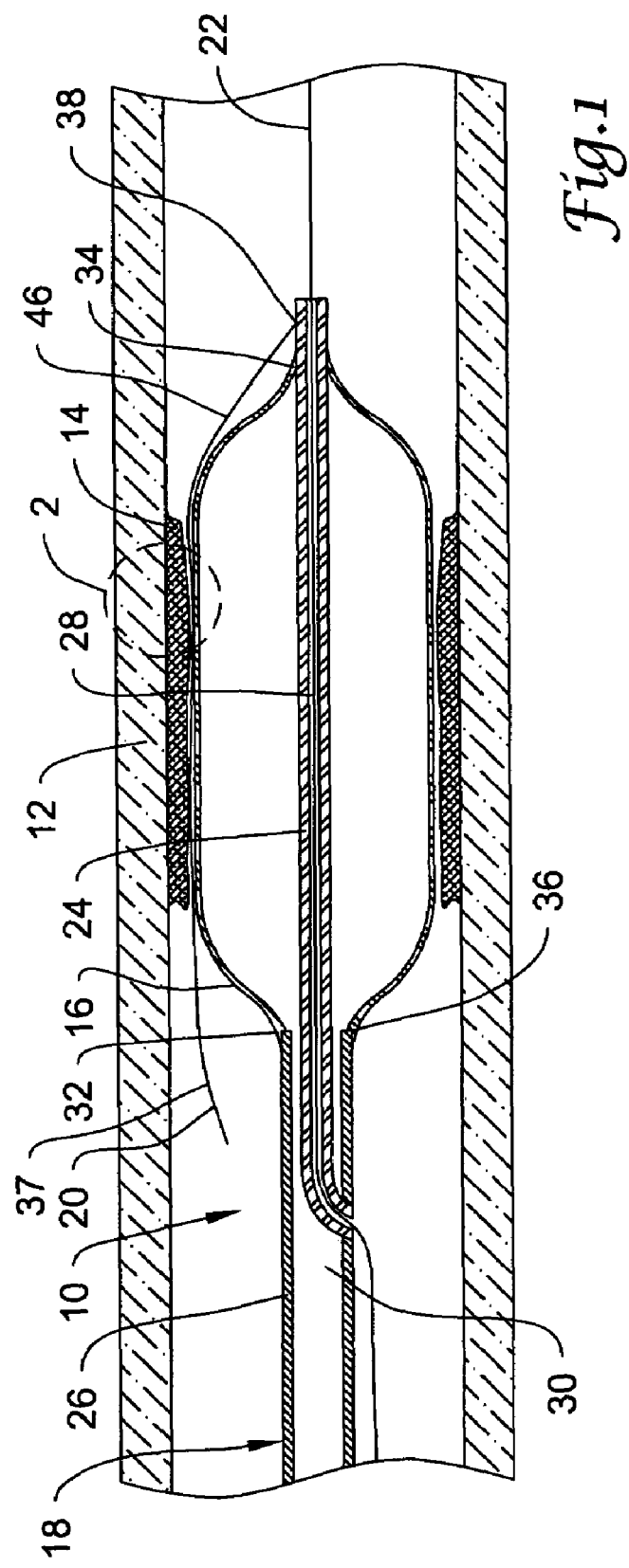
FIG. 1 is a partial cross-sectional side view of an example catheter disposed in a blood vessel.

The following description should be read with reference to the drawings wherein like reference numerals indicate like elements throughout the several views. The detailed description and drawings illustrate example embodiments of the claimed invention.

Angioplasty techniques have been shown to be effective for at least some intravascular interventions. FIG. 1 illustrates an example angioplasty catheter 10 positioned in a blood vessel 12 adjacent an intravascular lesion 14. Catheter 10 may include a balloon 16 coupled to a catheter shaft 18. A traction member 20 may be coupled to shaft 18 and/or balloon 16. In general, catheter 10 may be advanced over a guidewire 22 through the vasculature to a target area. Balloon 16 can then be inflated to expand lesion 14. The target area may be within any suitable peripheral or cardiac location.

In at least some embodiments, balloon 16 may be manufactured from a lubricious material. Alternatively, the balloon 16 may be coated with a lubricious material. Lubricity may be desirable for a number of reasons, such as to enhance the ability of balloon 16 to be navigated through the vasculature, particularly when advancing catheter 10 through a relatively narrow or occluded vessel. In these embodiments as well as other embodiments that utilize other balloon materials, a preferred embodiment of the present invention includes at least one traction member 20 to improve traction. In general, traction member 20 may be configured to improve the traction between balloon 16 and a target site (e.g., lesion 14) when using catheter 10. For example, balloon 16, because of its lubricity or for other reasons, could slip or move at the target site in a manner that is not unlike the way a watermelon seed might slip from a person's fingers when squeezed. Traction member 20 can provide a surface that can help maintain the position of balloon 16 and keep balloon 16 from slipping away from lesion 14 or the target site. Therefore, including traction member 20 can allow for greater control when positioning balloon 16 and may allow lesion 14 to be expanded more precisely. Some of the other features, characteristics, and alternative embodiments of traction member 20 are described in more detail below.

Balloon 16 may be made from typical angioplasty balloon materials including polymers such as polyethylene terephthalate (PET), polyetherimid (PEI), polyethylene (PE), etc. Some other examples of suitable polymers, including lubricious polymers, may include polytetrafluoroethylene (PTFE), ethylene tetrafluoroethylene (ETFE), fluorinated ethylene propylene (FEP), polyoxymethylene (POM), polybutylene terephthalate (PBT), polyether block ester, polyurethane, polypropylene (PP), polyvinylchloride (PVC), polyether-ester (for example, a polyether-ester elastomer such as ARNITEL® available from DSM Engineering Plastics), polyester (for example, a polyester elastomer such as HYTREL® available from DuPont), polyamide (for example, DURETHAN® available from Bayer or CRISTAMID® available from Elf Atochem), elastomeric polyamides, block polyamide/ethers, polyether block amide (PEBA, for example, available under the trade name PEBAX®), silicones, Marlex high-density polyethylene, Marlex low-density polyethylene, linear low density polyethylene (for example, REXELL®), polyetheretherketone (PEEK), polyimide (PI), polyphenylene sulfide (PPS), polyphenylene oxide (PPO), polysulfone, nylon, perfluoro(propyl vinyl ether) (PFA), other suitable materials, or mixtures, combinations, copolymers thereof, polymer/metal composites, and the like. In some embodiments, it may be desirable to use high modulus or generally stiffer materials so as to reduce balloon elongation. The above list of materials includes some examples of higher modulus materials. Some other examples of stiffer materials include polymers blended with liquid crystal polymer (LCP) as well as the materials listed above. For example, the mixture can contain up to about 5% LCP. Alternatively, the balloon may be coated with a relatively lubricious material such as a hydrogel or silicone.

Shaft 18 may be a catheter shaft, similar to typical catheter shafts. For example, shaft 18 may include an inner tubular member 24 and outer tubular member 26. Tubular members 24/26 may be manufactured from a number of different materials. For example, tubular members 24/26 may be made of metals, metal alloys, polymers, metal-polymer composites or any other suitable materials. Some examples of suitable metals and metal alloys include stainless steel, such as 304V, 304L and 316L stainless steel; nickel-titanium alloy such as linear-elastic or super-elastic Nitinol, nickel-chromium alloy, nickel-chromium-iron alloy, cobalt alloy, tungsten or tungsten alloys, MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si), hastelloy, monel 400, inconel 825, or the like; or other suitable material. Some examples of suitable polymers include those described above in relation to balloon 16. Of course, any other suitable polymer may be used without departing from the spirit of the invention. The materials used to manufacture inner tubular member 24 may be the same as or be different from the materials used to manufacture outer tubular member 26.

Tubular members 24/26 may be arranged in any appropriate way. For example, in some embodiments inner tubular member 24 can be disposed coaxially within outer tubular member 26. According to these embodiments, inner and outer tubular members 24/26 may or may not be secured to one another along the general longitudinal axis of shaft 18. Alternatively, inner tubular member 24 may follow the inner wall or otherwise be disposed adjacent the inner wall of outer tubular member 26. Again, inner and outer tubular members 24/26 may or may not be secured to one another. For example, inner and outer tubular members 24/26 may be bonded, welded (including tack welding or any other welding technique), or otherwise secured at a bond point. In some embodiments, the bond point may be generally disposed near the distal end of shaft 18. However, one or more bond points may be disposed at any position along shaft 18. The bond may desirably impact, for example, the stability and the ability of tubular members 24/26 to maintain their position relative to one another. In still other embodiments, inner and outer tubular member 24/26 may be adjacent to and substantially parallel to one another so that they are non-overlapping. In these embodiments, shaft 18 may include an outer sheath that is disposed over tubular members 24/26.

Inner tubular member 24 includes an inner lumen 28. In a preferred embodiment, inner lumen 28 is a guidewire lumen. Accordingly, catheter 10 can be advanced over guidewire 22 to the desired location. The guidewire lumen may be extended along essentially the entire length of catheter shaft 18 so that catheter 10 resembles traditional "over-the-wire" catheters. Alternatively, the guidewire lumen may extend along only a portion of shaft 18 so that catheter 10 resembles "single-operator-exchange" or "rapid-exchange" catheters. Regardless of which type of catheter is contemplated, catheter 10 may be configured so that balloon 16 is disposed over at least a region of inner lumen 28. In at least some of these embodiments, inner lumen 28 (i.e., the portion of inner lumen 28 that balloon 16 is disposed over) may be substantially coaxial with balloon 16.

Shaft 18 may also include an inflation lumen 30 that may be used, for example, to transport inflation media to and from balloon 16. The location and position of inflation lumen 30 may vary, depending on the configuration of tubular members 24/26. For example, when outer tubular member 26 is disposed over inner tubular member 24, inflation lumen 30 may be defined within the generally annular space between tubular members 24/26. Moreover, depending on the position of inner tubular member 24 within outer tubular member 26, the shape of lumen 30 (i.e., the shape adjacent shaft 18) may vary. For example, if inner tubular member 24 is attached to or disposed adjacent to the inside surface of outer tubular member 26, then inflation lumen 30 may be generally half-moon in shape; whereas if inner tubular member 24 is generally coaxial with outer tubular member 26, then inflation lumen 30 may be generally ring-shaped or annular in shape. It can be appreciated that if outer tubular member 26 is disposed alongside inner tubular member 24, then lumen 30 may be the lumen of outer tubular member 26 or it may be the space defined between the outer surface of tubular members 24/26 and the outer sheath disposed thereover.

Balloon 16 may be coupled to catheter shaft 18 in any of a number of suitable ways. For example, balloon 16 may be adhesively or thermally bonded to shaft 18. In some embodiments, a proximal waist 32 of balloon 16 may be bonded to shaft 18, for example, at outer tubular member 26, and a distal waist 34 may be bonded to shaft 18, for example, at inner tubular member 24. The exact bonding positions, however, may vary. It can be appreciated that a section of proximal waist 32 may not have section 36 extending therefrom in order for suitable bonding between balloon 16 and outer tubular member 30.

In addition to some of the structures described above, shaft 18 may also include a number of other structural elements, including those typically associated with catheter shafts. For example, shaft 18 may include a radiopaque marker coupled thereto that may aid a user in determining the location of catheter 10 within the vasculature. In addition, catheter 10 may include a folding spring (not shown) coupled to balloon 16, for example, adjacent proximal waist 32, which may further help in balloon folding and refolding. A description of a suitable folding spring can be found in U.S. Pat. Nos. 6,425,882 and 6,623,451, the disclosures of which are incorporated herein by reference.

The attachment point and/or attachment configuration of traction member 20 may vary. For example, traction member 20 can be attached to shaft 18. In at least some of these embodiments, the distal end 38 of traction member 20 may be attached to shaft 18 at a position distal of balloon 16. However, this configuration is not intended to be limiting as essentially any part of traction member 20 may be attached to shaft 18 at essentially any suitable position. The type of attachment may also vary. For example, traction member 20 may be attached to shaft 18 by welding, laser bonding, soldering, brazing, adhesive bonding, by using a mechanical fitting or connector, by winding or wrapping traction member 20 around shaft 18, and the like, or in any other suitable way.

As stated above, traction member 20 may be configured to improve the traction between catheter 10 (i.e., balloon 16) and lesion 14. In some embodiments, traction can be improved by virtue of traction member 20 being disposed alongside at least a portion of balloon 16. In addition to being disposed alongside balloon 16 or in the alternative, traction can be improved by including a gripping region or set of gripping members 40 along traction member 20 (more clearly seen in FIG. 2). The form or configuration of traction member 20 and/or gripping region 40 may vary. For example, gripping region or members 40 may take the form of a surface refinement that can enhance the traction generated by traction member 20. Alternatively, gripping region 40 may be a region of traction member 20 that has a shape or configuration that is adapted to enhance traction. Some examples of suitable traction members 20 and gripping regions 40 are described in more detail below.

Figure 2:
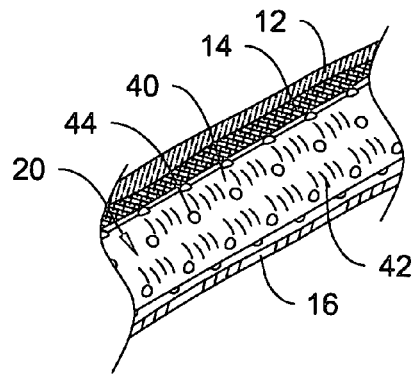
FIG. 2 is an enlarged perspective view of a portion of the catheter shown in FIG. 1 that shows some of the features of the traction member.

FIG. 2 illustrates an enlarged view of traction member 20 that more clearly shows gripping region 40. According to this embodiment, gripping region 40 can be defined by a textured surface 42 and/or series of bumps or projections 44 disposed along traction member 20. Textured surface 42 can be formed or defined in any suitable manner. For example, textured surface 42 can be formed by scoring, grinding, scuffing, or otherwise altering traction member 20. The pattern of textured surface 42 may also vary and can be random, regular, intermittent, or any other suitable pattern.

Similarly, bumps 44 may be formed, defined, or attached to traction member 20 in any suitable manner. For example, bumps 44 (and/or textured surface 42) may be defined by grinding traction member 20. Alternatively, bumps 44 may be molded, bonded, or otherwise attached to traction member 20 in any suitable way. The pattern may also be random, regular, or intermittent. For example, bumps 44 may be disposed along only a portion of the surface area of traction member such as the outward-facing surface (i.e., the surface facing away from balloon 16). Bumps 44 may have any suitable shape. For example, bumps may be rounded or cylindrical, squared, triangular or pyramidal, polygonal, pointed, blunted, and the like, or any other suitable shape.

In general, gripping region 40 (i.e., textured region 42 and/or bumps 44 that define gripping region 40) may be disposed along the entire length of traction member 20 or along any portion thereof. For example, gripping region 40 may be disposed along a body portion 46 (shown in FIG. 1) of the traction member which extends over the expanding portion of the balloon, then contacts the lesion. Body portion 46 is defined as a section of traction member 20 disposed between distal end region 38 and a proximal end region 37 of traction member 20. Accordingly, gripping region 40 can be positioned between distal end region 38 and the proximal end region. As suggested above, however, gripping region 40 can be disposed along any portion of traction member 20 including along distal end region 38, a body portion 46, a proximal end region 37, or combinations thereof. Moreover, gripping region 40 need not be disposed in a continuous arrangement and may be disposed intermittently or in any other suitable arrangement. For example, gripping region 40 may include textured surface 42 without bumps 44 followed by textured surface 42 with bumps 44, with or without a space therebetween.

Figure 3:
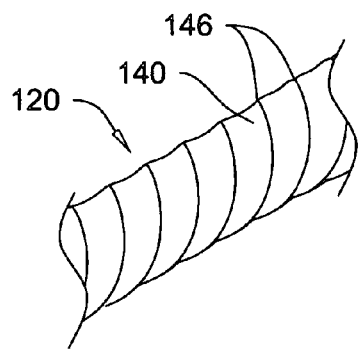
FIG. 3 is a partial perspective view of a portion of another example traction member.
Figure 4:
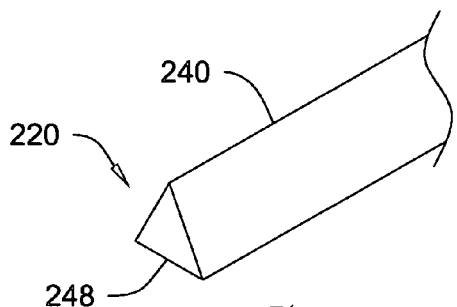
FIG. 4 is a partial perspective view of a portion of another example traction member.

FIGS. 3-7 illustrate alternative example embodiments of traction members that include various example gripping regions. For example, FIG. 3 illustrates traction member 120 having gripping region 140 that is defined by a twist or helical winding formed in traction member 120. The twist or winding may define a series of peaks or ridges 146 in traction member 120 that can "grip" both balloon 16 and lesion 14 or otherwise help maintain the position of balloon 16 relative to lesion 14. The twist can be formed in traction member 120 in any suitable manner and may be continuous, intermittent, have a regular or irregular pitch, or configured in any suitable manner. A number of additional shapes and configurations can be used in alternative embodiments. For example, FIG. 4 illustrates another example traction member 220 that includes a pointed and longitudinally extending gripping region 240. This embodiment has a triangular cross-sectional shape and a base side 248 that can be disposed, for example, is adjacent balloon 16. Of course, other shapes can be used in various forms of traction members without departing from the spirit of the invention. For example, various embodiments of traction members may have circular, square, rectangular, polygonal, or any other suitable cross-sectional shape.

Figure 5:
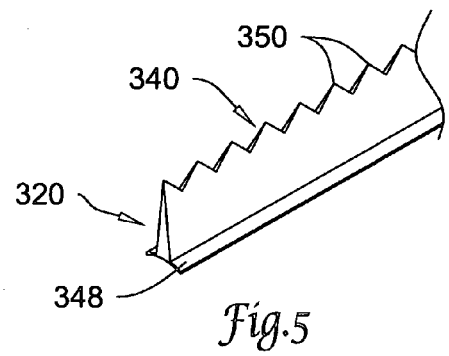
FIG. 5 is a partial perspective view of a portion of another example traction member.
Figure 6:
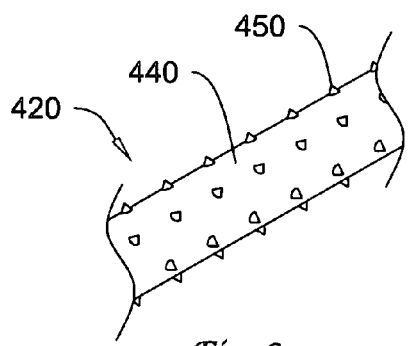
FIG. 6 is a partial perspective view of a portion of another example traction member.

Traction member 320, illustrated in FIG. 5, includes a saw-tooth shaped gripping region 340. The saw-tooth gripping region may be characterized by a plurality of triangular or pyramidal teeth 350 extending outward from traction member 320. Teeth 350 may allow traction member 320 to grip or otherwise maintain its position relative to lesion 14. In addition, traction member 320 may include a base 348 that is adapted to contact and grip balloon 16. In some embodiments, base 348 may include a textured surface or other structural refinement that improves traction between base 348 and balloon 16. Similarly, FIG. 6 illustrates traction member 420 that includes gripping region 440 having a plurality of spikes or teeth 450. Teeth 450 may be disposed along essentially the entire surface area of traction member 420 so that teeth 450 can grip both balloon 16 and lesion 14 and improve traction therebetween. The dispersal pattern and shape of teeth 450 can vary to include any suitable arrangement.

Figure 7:
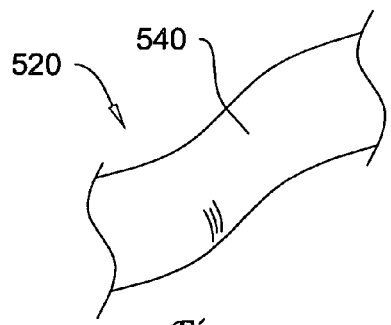
FIG. 7 is a partial perspective view of a portion of another example traction member.

FIG. 7 illustrates another example traction member 520 that includes gripping region 540 that is defined by a curve or undulation in traction member 520. The undulation may curve in any suitable manner and in any suitable direction or combination of directions. For example, gripping region 540 may include an undulation that curves from side-to-side, up-and-down, any direction between side-to-side and up-and-down, combinations thereof, or in any other suitable manner. The degree of curvature, pattern of curvature, and positioning of curves along the length of traction member 520 may also vary to include essentially any appropriate configuration.

Figure 8:
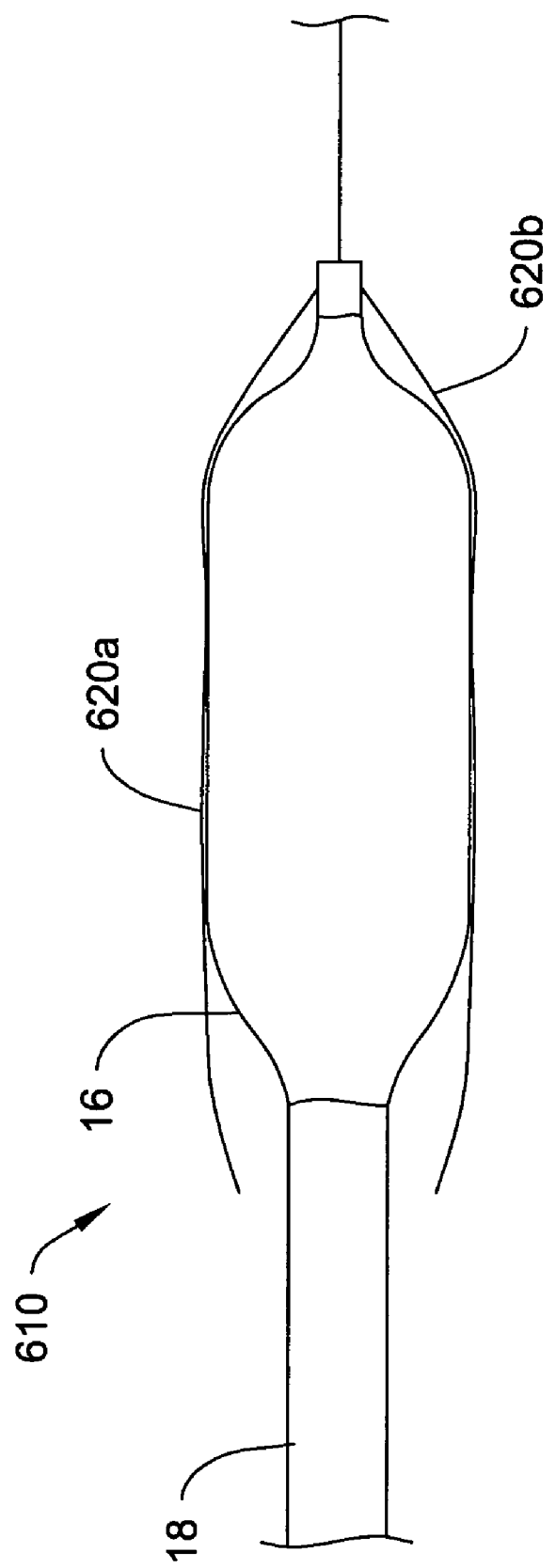
FIG. 8 is a simplified schematic side view of another example catheter.
Figure 9:
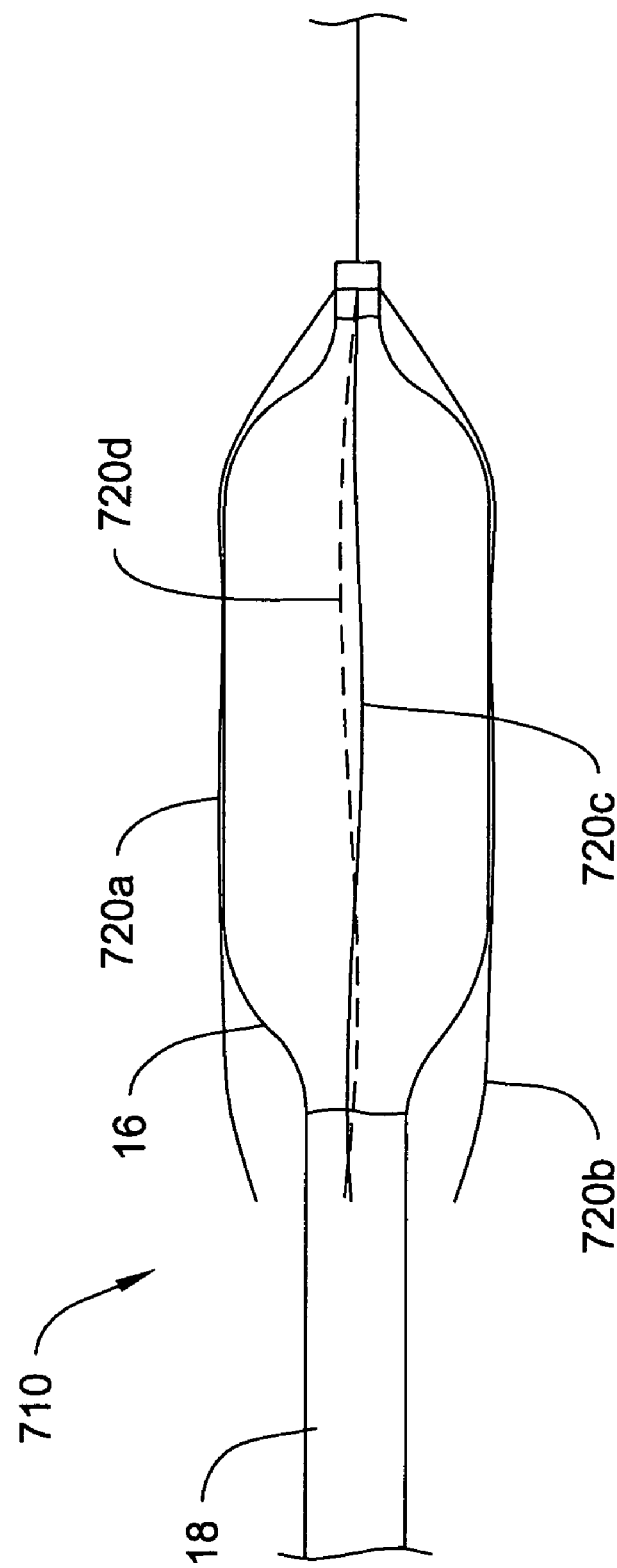
FIG. 9 is a simplified schematic side view of another example catheter.
Figure 10:
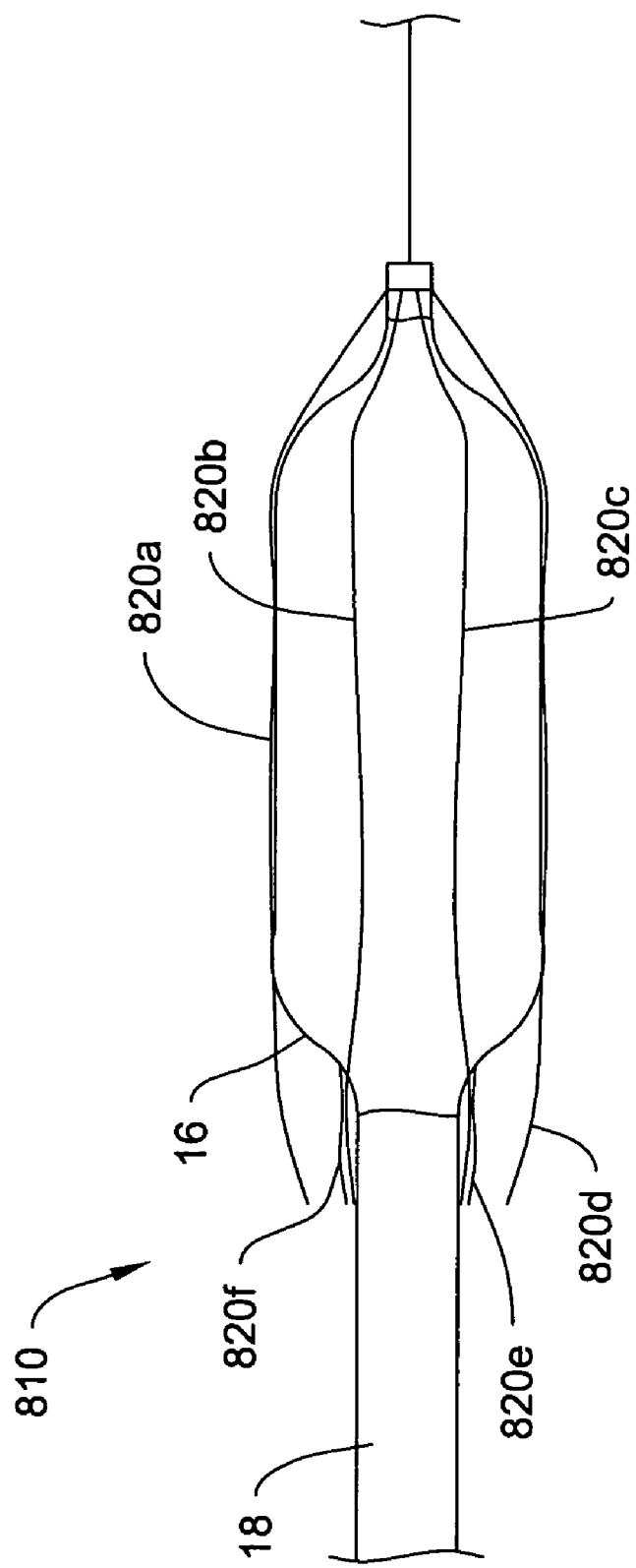
FIG. 10 is a simplified schematic side view of another example catheter.

Although the foregoing figures illustrate various example catheters having one traction member, the invention is not intended to be limited to any particular number of traction members. FIGS. 8-10 depict example devices with varying numbers of traction members. For example, FIG. 8 illustrates catheter 610 having two traction members 620*a*/620*b*. Similarly, FIG. 9 illustrates catheter 710 having four traction members 720*a*/*b*/*c*/*d* and FIG. 10 illustrates catheter 810 having six traction members 820*a*/*b*/*c*/*d*/*e*/*f*. From these figures it can seen that a variation in the number of traction members is contemplated and may be one or more, two or more, three or more, four or more, five or more, six or more, and so on. Moreover, embodiments that include a plurality of traction members may include a plurality of the same or similar traction members or combination of differing traction member embodiments, including any of those described herein.

Figure 11:
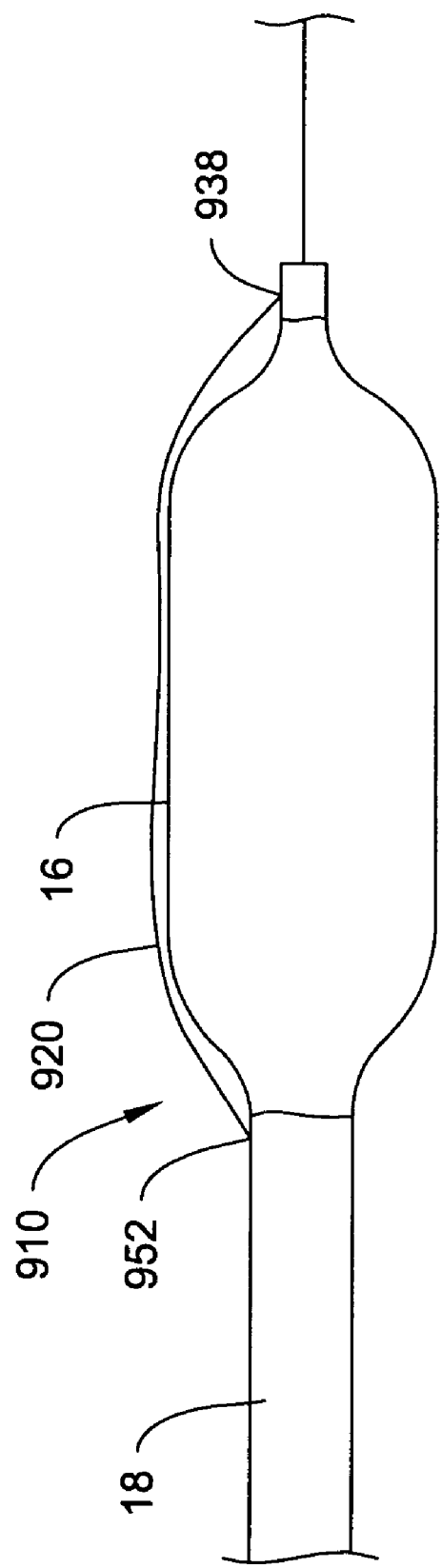
FIG. 11 is a simplified schematic side view of another example catheter.

FIGS. 11 and 12 demonstrate that any of the traction members described above may be attached to the catheter in a variety of ways and at a variety of positions. For example, FIG. 1 illustrates that distal end 38 of traction member 20 may be attached to shaft 18 at a position distal of balloon 16. According to this embodiment, the proximal end of traction member 20 is not directly attached to the catheter. The embodiments depicted in FIGS. 11 and 12 illustrate situations where the proximal end of a traction member may be directly attached to the catheter. For example, catheter 910 in FIG. 11 may include traction member 920 with both its distal end 938 and its proximal end 952 attached to shaft 18. Similarly, catheter 1010 in FIG. 12 includes traction member 1020 with both its distal end 1038 and its proximal end 1052 attached to balloon 16.

FIGS. 13-15 depict additional embodiments that illustrate that the positioning of the proximal end of the traction member may also vary. For example, FIG. 13 illustrates catheter 1110, which includes traction member 1120 with proximal end 1152 disposed adjacent the proximal waist 32 of balloon 16. Similarly, FIG. 14 illustrates catheter 1210 having proximal end 1252 of traction member 1220 disposed near the mid-region of balloon 16, and FIG. 15 illustrates catheter 1310 having proximal end 1352 of traction member 1320 disposed near distal waist 34 of balloon 16.

The representative embodiments show the traction member 20 extending longitudinally. It is, however, contemplated that any or all of the traction members may extend over any portion of the balloon in an alternative direction. For example, a traction member may extend radially around the balloon. Alternatively, it may follow a generally helical pattern over the balloon.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A balloon catheter, comprising:
    an elongate catheter shaft having a distal end, an inflation lumen defined therein and a guidewire lumen defined therein;
    a balloon coupled to the shaft and disposed adjacent the distal end of the shaft, the balloon being substantially coaxially arranged with at least a region of the guidewire lumen;
    wherein the balloon has an expansion region that contacts a blood vessel wall during use of the balloon;
    a non-woven traction member positioned exterior of the balloon, the traction member having a distal end affixed to the balloon catheter at a position proximate the distal end of the shaft and extending in the proximal direction and a proximal end that is unattached to the balloon catheter, the traction member being configured to provide traction between the balloon and a target site, wherein the traction member includes a section that extends over the expansion region of the balloon and wherein at least the section of the traction member extending over the expansion region conforms with the expansion region during use of the balloon;
    wherein the traction member includes a gripping region defined along at least a portion thereof; and
    wherein the gripping region is defined by one or more bumps disposed on the traction member.

* * * * *